United States Patent [19]

Thummel et al.

[11] 4,414,158

[45] Nov. 8, 1983

[54] PHOSPHONOMETHYLGLYCYLHYDROXAMIC ACID AND NOVEL HERBICIDALLY ACTIVE SALTS THEREOF

[75] Inventors: Rudolph C. Thummel, Courgenay; Hanspeter Fischer, Bottmingen; Ludwig Maier, Arlesheim, all of Switzerland

[73] Assignee: Ciba-Geigy Corporation, Ardsley, N.Y.

[21] Appl. No.: 255,411

[22] Filed: Apr. 20, 1981

[30] Foreign Application Priority Data

Apr. 29, 1980 [CH] Switzerland .................. 3302/80

[51] Int. Cl.³ .......................... C07F 1/08; C07F 9/38
[52] U.S. Cl. .................. 260/438.1; 260/500.5 H; 260/502.5 F; 260/501.15; 260/501.21; 546/22; 71/86
[58] Field of Search ............ 260/500.5 H, 502.5, 260/501.15, 501.21, 438.1; 71/86; 546/22

[56] References Cited

U.S. PATENT DOCUMENTS 3,919,360  11/1975  Collins .................. 260/500.5 H

FOREIGN PATENT DOCUMENTS 7210  1/1980  European Pat. Off. .
39310  11/1981  European Pat. Off. .
2152826  7/1974  Fed. Rep. of Germany .

OTHER PUBLICATIONS

H. Henecka et al., "Funktionelle N-Derivate der Carboxylgruppe," Houben-Weyl vol. 8, pp. 684–692.
J. Franz, "Glyphosate and Related Chemistry", pp. 139–147.
Abstract of Japanese Pat. No. 79-36653.

*Primary Examiner*—Anton H. Sutto
*Attorney, Agent, or Firm*—Frederick H. Rabin

[57] ABSTRACT

The invention relates to N-phosphonomethylglycylhydroxamic acid of the formula I

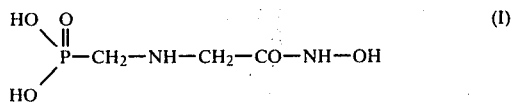

or of the tautomeric formula Ia

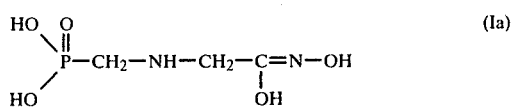

and salts thereof with strong acids, organic nitrogen bases, alkali metal or alkaline earth metal ions, as well as complex salts with aluminium or heavy metal compounds. These compounds have herbicidal and plant growth-regulating properties.

8 Claims, No Drawings

PHOSPHONOMETHYLGLYCYLHYDROXAMIC ACID AND NOVEL HERBICIDALLY ACTIVE SALTS THEREOF

The present invention relates to N-phosphonomethylglycylhydroxamic acid and herbicidally active salts thereof, to the production thereof, to compositions containing them, and to their use as herbicides.

The N-phosphonomethylglycylhydroxamic acid of this invention has the formula I

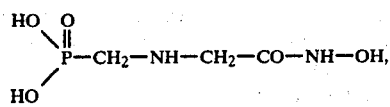

and/or the tautomeric formula Ia

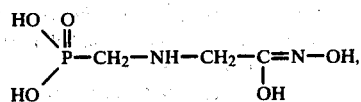

The invention also comprises the salts of this compound with strong acids, organic nitrogen bases, alkali metal or alkaline earth metal ions, and complex salts with aluminium or heavy metal compounds.

Examples of strong acids suitable for the salt formation are mineral acids such as hydrochloric acid, hydrobromic acid, hydriodic acid, sulfuric acid, nitric acid, phosphoric acid, and also organic acids such as sulfonic acids, halosulfonic acids or haloacetic acids. Preferred acids, however, are hydrochloric and hydrobromic acid.

Examples of organic nitrogen bases suitable for the salt formation are primary, secondary and tertiary aliphatic and aromatic amines such as methylamine, ethylamine, propylamine, isopropylamine, the four isomeric butylamines, dodecylamine, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline, isoquinoline etc., preferably ethyl-, propyl-, diethyl- or triethylamine, but, most preferably, isopropylamine; pyridinium cations such as 1-methyl-4,4'-bipyridinium cation, the 4-pyrrolidinium-pyridinium dication, and tetraalkylammonium cations the alkyl moieties of which, each independently of the other, are identical or different, straight-chain or branched alkyl radicals of 1 to 12 carbon atoms, preferably straight-chain, and are benzyl.

Preferred salt-forming alkali metal and alkaline earth metal ions are lithium, sodium, potassium, magnesium or calcium, with sodium or potassium being most preferred. Examples of heavy metals which form complex salts are chromium, manganese, iron, nickel, copper, zinc, tin, mercury and lead.

The preferred compound is that of the formula I or Ia as free acid, mono-, di- or trisodium salt, copper salt, isopropylammonium salt, tetrabutylammonium salt, 4-pyrrolidinium-pyridinium salt, 1-methyl-4,4'-bipyridinium salt, dimethylbenzylammonium salt, dimethyldodecylammonium salt, or as hydrohalide.

Among this group of preferred compounds, the free acid, the mono- and disodium salt, the copper salt, the isopropylammonium salt and the hydrohalides are particularly preferred. The most preferred compound is the free acid.

The N-phosphonomethylglycylhydroxamic acid of the formula I and/or Ia is obtained by methods which are known per se. A first method of obtaining the compound of the formula I or Ia is in accordance with the procedure described in Houben-Weyl, 4th edition, Methoden der organischen Chemie 8, 684, by reacting a N-phosphonomethylglycine compound of the formula II

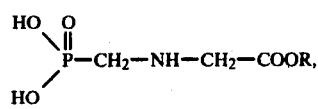

wherein R is hydrogen or $C_1$-$C_4$alkyl, in the presence of a base, with hydroxylamine of the formula III

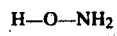

The compound of the formula I or Ia can also be obtained in accordance with the procedure described by J. E. Franz, Adv. in Pesticide Science, Zürich 1978, Pergamon Press, ed. H. Geissbühler, Symp. Papers, 4th Int. Cong. Pest. Chem., page 139, by heating glycylhydroxamic acid of the formula IV

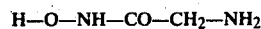

in the presence of hydrochloric acid or hydrobromic acid, with formaldehyde and phosphorous acid.

A further method of obtaining the compound of the formula I or Ia comprises reacting glycylhydroxamic acid of the formula IV, in the presence of an acid acceptor, with a halomethylphosphonic acid of the formula V

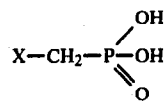

wherein X is chlorine or bromine, in accordance with a procedure described in German Auslegeschrift 2 152 826.

Yet a further method of obtaining the compound of the formula I or Ia comprises reacting a halide of the formula VI

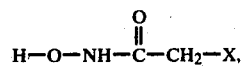

wherein X is chlorine or bromine, in the presence of an acid acceptor, with an aminomethylphosphonic acid of the formula VII

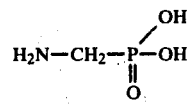

The compounds of the invention can also be obtained in accordance with the particulars of J. E. Franz, ibid., by oxidising the phosphonous acid of the formula VIII

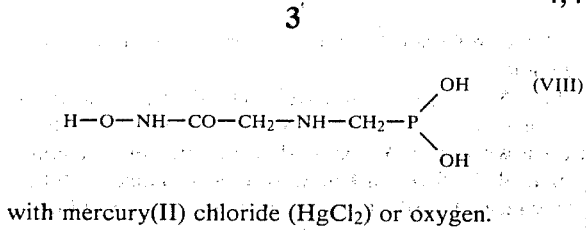

with mercury(II) chloride (HgCl$_2$) or oxygen.

The compound of the formula I or Ia can further be obtained by heating a hexahydrotriazine of the formula IX

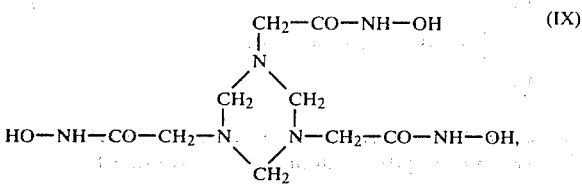

which is obtained from glycylhydroxamic acid of the formula IV and formaldehyde, with a dialkylphosphite of the formula X

and hydrolysing the resultant phosphonic acid ester of the formula XI

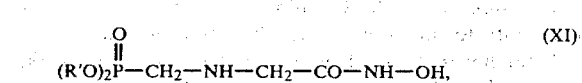

wherein R' is C$_1$-C$_4$alkyl.

Finally, the compound of the formula I can also be obtained by heating an amino acid derivative of the formula XII

wherein R'' is benzyl, benzhydryl or triphenylmethyl, in the presence of hydrochloric acid or hydrobromic acid, with formaldehyde and phosphorous acid or phosphorus trichloride which gives phosphorous acid in water, and when the reaction is complete, removing the group R'' either with hydrobromic acid at elevated temperature (140°-180° C.) or with hydrogen in the presence of catalytic amounts of 5% palladium on carbon.

The free acids of the formula I or Ia obtainable by the different methods can be converted, if desired, into their salts by methods known per se.

It is known to use N-phosphonomethylglycine (glyphosate) and its ammonium, alkali metal and alkaline earth metal salts and a number of heavy metal salts, amides, esters and phenylhydrazides as well as N-trifluoroacetyl derivatives, as contact herbicides, from J. E. Franz, ibid., and from German Auslegeschrift 2 152 826, Japanese patent publication No. 79 036 653, U.S. Pat. No. 4,180,394 and European patent application 7210.

The N-phosphonomethylglycylhydroxamic acid of this invention and its salts are novel and have excellent herbicidal activity in pre-emergence, but especially in postemergence, application.

In addition, the compound of the formula I or Ia influences plant growth in various ways. For example, the root growth of cereals is stimulated.

The compound of the formula I or Ia or its salts are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I or Ia and, where appropriate, a solid or liquid adjuvant, are prepared in known manner, e.g. by homogeneously mixing and/or grinding the active ingredients with extenders, e.g. solvents, solid carriers and, where appropriate, surfactants.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising surfactant mixtures.

Suitable anionic surfactants can be both water-soluble soaps and water-soluble synthetic surface-active compounds.

Suitable soaps are the alkali, alkaline earth or unsubstituted or substituted ammonium salts of higher fatty acids (C$_{10}$-C$_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali, alkaline earth or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide, adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$-$C_{22}$alkyl radical and, as further substituents, lower unsubstituted or halogenated alkyl, benzyl or lower hydroxyalkyl radicals or fatty acid. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ringwood, N.J., 1979; Sisely and Wood, "Encyclopedia of Surface Active Agents", Chemical Publishing Co. Inc., New York, 1964.

When formulating the compound of the formula I or Ia or the corresponding salts, it is particularly advantageous to add inorganic salts, e.g. sodium chloride or potassium chloride.

The pesticidal formulations usually contain 0.1 to 99%, preferably 0.1 to 95%, of a compound of the formula I or Ia, 1 to 99.9% of a solid or liquid adjuvant, and 0 to 25%, preferably 0.1 to 25%, of a surfactant.

Preferred formulations are composed in particular of the following constituents (% = percentage by weight):

Solutions active ingredient: 5 to 95%, preferably 10 to 80%
solvent: 95 to 5%, preferably 90 to 0%
surfactants: 1 to 30%, preferably 2 to 20%

Emulsifiable concentrates active ingredient: 10 to 50%, preferably 10 to 40%
surfactant: 5 to 30%, preferably 10 to 20%
liquid carrier: 20 to 95%, preferably 40 to 80%

Dusts active ingredient: 0.5 to 10%, preferably 2 to 8%
solid carrier: 99.5 to 90%, preferably 98 to 2%

Suspension concentrates active ingredients: 5 to 75%, preferably 10 to 50%
water: 94 to 25%, preferably 90 to 30%
surfactant: 1 to 40%, preferably 2 to 30%

Wettable powders active ingredient: 5 to 90%, preferably 10 to 80% and, most preferably, 20 to 60%
surfactant: 0.5 to 20%, preferably 1 to 15%
solid carrier: 5 to 90%, preferably 30 to 70%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.25 to 5 kg a.i./ha.

The formulations can also contain further additives such as stabilisers, antifoams, viscosity regulators, binders, adhesives, as well as fertilisers or other active compounds, in order to attain special effects. Accordingly, in addition to containing the compounds of the general formula I or Ia or their salts, the compositions of the invention can also contain e.g. insecticides, fungicides, bactericides, fungistats, bacteriostats, nematocides or further herbicides, in order to broaden the activity spectrum.

The invention is further illustrated by the following Examples.

PREPARATORY EXAMPLES

Example 1: N-phosphonomethylglycylhydroxamic acid with 5 moles of NaCl

A mixture of 10 g (0.05 mole) of ethyl N-phosphonomethylglycinate, 7 g (0.1 mole) of hydroxylamine hydrochloride and 15 g (0.25 mole) of sodium methylate in 200 ml of methanol is stirred for 15 hours and then 30 ml of a 5 N solution of HCl in methanol are added. The precipitate is isolated by filtration, washed repeatedly with methanol and dried, affording 5 g of a colourless powder which decomposes at 60°-70° C. with foaming and has the composition of N-phosphonomethylglycylhydroxamic acid with 5 moles of NaCl (compound 1).

Analysis: $C_3H_9N_2O_5 + 5$ NaCl—calculated: C 7.56, H 1.98, N 5.88, P 6.51, Na 24.13, Cl 37.25; found: C 7.5, H 2.0, N 5.6, P 6.3, Na 24.4, Cl 37.3.

With iron(III) ions the compound gives the characteristic red coloration of hydroxamic acids.

Example 2: Disodium salt of N-phosphonomethylglycylhydroxamic acid

To a solution of 27.5 g (0.15 mole) of methyl N-phosphonomethylglycinate in 700 ml of methanol is added a solution of 0.3 mole of hydroxylamine in 300 ml of methanol, which is obtained by adding a solution of 6.9 g (0.3 gram-atoms) of sodium in 200 ml of methanol to a suspension of 21 g (0.3 mole) of hydroxylamine hydrochloride and filtering off the NaCl precipitate. To this solution is further added a solution of 6.9 g (0.3 gram-atoms) of sodium in 250 ml of methanol until the reaction solution is alkaline to phenolphthalein. After a reaction time of 16 hours the disodium salt of N-phosphonomethylglycylhydroxyamic acid is obtained in 95% yield in the form of a finely crystalline colourless powder which does not melt below 210° C. (compound 2).

Analysis: $C_3H_7N_2Na_2O_5P$—calculated: C 15.8, H 3.1, N 12.3, Na 20.2, P 13.6; found: C 15.6, H 3.3, N 11.5, Na 19.5, P 13.0, Cl 0.3.

Example 3: N-phosphonomethylglycylhydroxamic acid 4.6 g (0.02 mole) of the disodium salt of N-phosphonomethylglycylhydroxaimic acid are dissolved in 40 ml of aqueous 1 N HCl solution, whereupon N-phosphonomethylglycylhydroxamic acid precipitates rapidly in the form of a finely crystalline colourless powder which decomposes at 186° C. with foaming. After washing with water and methanol and drying in vacuo at 60° C., the product is obtained in 90% yield (compound 3).

Analysis: $C_3H_9N_2O_5P$—calculated: C 19.58, H 4.93, N 15.22, P 16.83; found: C 19.5, H 5.0, N 15.0, P 16.8.

Example 4: N-phosphonomethylglycylhydroxamic acid hydrochloride 4.6 g (0.02 mole) of the dissodium salt of N-phosphonomethylglycylhydroxamic acid are dissolved in 20 ml of a 5 N solution of HCl in methanol and the solution is stirred for ½ hour. Precipitated NaCl is then filtered off and the solution is evaporated in vacuo. Remaining solvent is removed in a high vacuum at 40° C./0.1 mbar, affording N-phosphonoglycylhydroxamic acid hydrochloride in a yield of 60% in the form of a tacky resin (compound 4).

Example 5: Copper salt of N-phosphonomethylglycylhydroxamic acid

Excess copper(II) acetate solution is added to an aqueous solution of 1.5 g of N-phosphonomethylglycylhydroxamic acid with 5 moles of NaCl. The bluish-green precipitate which forms at once is isolated, decocted with water and dried, affording 1.3 g of a green powder which does not melt in the temperature range up to 200° C. and has the composition $[(C_3H_8N_2O_5P)_2]^{2-}Cu^{2+}$ (compound 5).

Example 6: N-phosphonomethylglycylhydroxamic acid 1.3 g of N-phosphonomethylglycylhydroxamic acid copper salt $[(C_3H_8N_2O_5P)_2]^{2-}Cu^{2+}$ are suspended in 50 ml of ethanol. The mixture is saturated with hydrogen sulfide and stirred for 16 hours at 20° C. The black precipitate, which consists of N-phosphonomethylglycylhydroxamic acid and copper sulfide, is isolated by filtration and dried. This precipitate is stirred in a solution of 3 g of isopropylamine in 20 ml of ethanol, then non-dissolved copper sulfide is removed by filtration and 1 g of N-phosphonomethylglycylhydroxamic acid is precipitated from the solution with a solution of HCl in alcohol. The product is a colourless powder which decomposes at 130°-135° C. (compound 3).

After recrystallisation from water the compound is obtained in the form of colourless prisms which decompose at 192° C.

Example 7: Isopropylammonium salt of N-phosphonomethylglycylhydroxamic acid 1.7 g (0.01 mole) of N-phosphonomethylglycylhydroxamic acid are dissolved in 10 ml of methanol by adding 1.8 g (0.03 mole) of isopropylamine. The solution is concentrated in vacuo and the residue solidifies to a glassy foam. Yield: 2.6 of the isopropylamine salt of N-phosphonomethylglycylhydroxamic acid in the form of a white amorphous powder which begins to decompose from 70° C.

The following table lists compounds of the formula I or Ia obtained in accordance with Examples 1 to 7, as well as corresponding salts and also further salts which are obtainable in analogous manner.

| Compound | formula I or Ia | (°C.) Physical data |
|---|---|---|
| 1 | $(HO)_2PO-CH_2-NH-CH_2-CO-NH-OH + 5\ NaCl$ | m.p. 60–70° (decomp) |
| 2 | $[O_3P-CH_2-NH-CH_2-CO-NH-OH]^{2\ominus}2Na^{\oplus}$ | m.p. >210° |
| 3 | $(HO)_2PO-CH_2-NH-CH_2-CO-NH-OH$ | m.p. 192° (decomp) |
| 4 | $(HO)_2PO-CH_2-\overset{\oplus}{N}H_2-CH_2-CO-NH-OH\ Cl^{\ominus}$ | resin |
| 5 | $[(HO)_2PO-CH_2-NH-CH_2-CO-NH-O]_2^{\ominus}Cu^{2\oplus}$ | m.p. >200° |
| 6 | $[(HO)OPO-CH_2-NH-CH_2-CONH-OH]^{\ominus}H_3\overset{\oplus}{N}-iC_3H_7$ | m.p. 70° (decomp) |

-continued

| Compound | formula I or Ia | (°C.) Physical data |
|---|---|---|
| 7 | $[O_3P-CH_2-NH-CH_2-CONH-OH]^{2\ominus}$ [pyridinium-NH⊕ with N-H⊕ structure] | |
| 8 | $[O_3P-CH_2NH-CH_2-CO-NH-OH]^{2\ominus}2$ $[(CH_3)_2\overset{\oplus}{N}(CH_3)CH_2C_6H_5]$ | |
| 9 | $[O_3P-CH_2-NH-CH_2-CO-NH-OH]^{2\ominus}2$ $[(CH_3)_2\overset{\oplus}{N}H\text{-}nC_{12}H_{25}]$ | |
| 10 | $[(NaO)OPO-CH_2-CO-NH-OH]^{\ominus}$ [4,4'-bipyridinium, N-CH$_3$⊕] | |
| 11 | $[(HO)OPO-CH_2-NH-CH_2-CO-NH-OH]^{\ominus}Na^{\oplus}$ | |
| 12 | $[O_3P-CH_2-NH-CH_2-CO-NH-O]^{3\ominus}3Na^{\oplus}$ | |
| 13 | $[O_3P-CH_2-NH-CH_2-CONHOH]^{2\ominus}2^{\oplus}N(C_4H_9)_4$ | |

FORMULATION EXAMPLES

Example 8

Formulation Examples for liquid active ingredients of the formula I (throughout, percentages are by weight)

| (a) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Dusts which are ready for use are obtained by intimately mixing the carriers with the active ingredient.

Example 9

Formulation examples for solid active ingredients of the formula I (throughout, percentages are by weight)

| (a) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalene-sulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (d) Extruder granulate | |
|---|---|
| active ingredient | 10% |
| sodium lignosulfonate | 2% |
| Carboxymethylcellulose | 1% |
| kaolin | 87%. |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES

Example 10

Preemergence herbicidal action

In a greenhouse, immediately after sowing the test plants in seed dishes, the surface of the soil is treated with an aqueous dispersion of test compound, obtained from a 25% emulsifiable concentrate or from a 25% wettable powder with active ingredients which, on account of their insufficient solubility, cannot be processed to an emulsifiable concentrate. The seed dishes are kept in the greenhouse at 22°–25° C. and 50–70% relative humidity, and the test is evaluated after 3 weeks.

In this test the compounds of formula I exhibited a good herbicidal action against the monocot and dicot weeds at a rate of application of 4 kg a.i./ha.

Example 11

Postemergence herbicidal action (contact herbicide)

A number of weeds in pots, both monococts and dicots, are sprayed postemergence, in the 4- to 6-leaf stage, with an aqueous active ingredient dispersion at a rate of application of 4 kg a.i./ha, and then kept at 24°–26° C. and 45–60% relative humidity. The test is evaluated at least 15 days after treatment and the results are assessed in accordance with the following rating:

1 = plants totally withered
2–3 = very pronounced action
4–6 = medium action
7–8 = insignificant action
9 = no action (as untreated controls)

Postemergence action

Rat of application: 4 kg a.i./ha

| Com-pound | Avena | Setaria | Lolium | Solanum | Sinapis | Stellaria |
|---|---|---|---|---|---|---|
| 1 | 1 | 2 | 2 | 2 | 2 | 2 |
| 2 | 3 | 2 | 3 | 2 | 2 | 3 |
| 3 | 2 | 1 | 2 | 2 | 1 | 2 |

Example 12: Stimulation of root growth

Seeds of the "Raineri" hard wheat variety are tested with a suspension of the active ingredient. The rates of application are from 4 to 1670 mg of active ingredient per kg of seeds. The seeds are then cultivated in sterilised soil for 9 days in a climatic chamber at 15°–20° C. and 75% relative humidity. The length and dry weight of the roots of the seedlings are then determined in comparison to untreated controls.

In this test the compounds of the formula I or Ia and their salts increased both the length and weight of the roots by at least 10%.

What is claimed is:

1. An N-phosphonomethylglycylhydroxamic acid of the formula

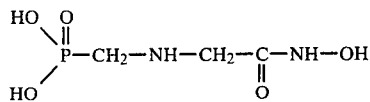

and/or the tautomeric formula $$\begin{array}{c}HO\quad O\\ \diagdown\|\\ P-CH_2-NH-CH_2-C=N-OH\\ \diagup\qquad\qquad\qquad|\\ HO\qquad\qquad\qquad\qquad OH\end{array}$$

in the form of the free acid, the mono-, di- or trisodium salt, the copper salt, the isopropylammonium salt, the tetrabutylammonium salt, the 4-pyrrolidinium-pyridinium salt, the 1-methyl-4,4'-bipyridinium salt, the dimethylbenzylammonium salt, the dimethyldodecylammonium salt, or of a hydrohalide.

2. A compound according to claim 1 in the form of the free acid, the mono- or disodium salt, the copper salt, the isopropylammonium salt, or of a hydrohalide.

3. N-phosphonomethylglyclhydroxamic acid according to claim 2.

4. The monosodium salt of a N-phosphonomethylglycylhydroxamic acid according to claim 2.

5. The disodium salt of a N-phosphonomethylglycylhydroxamic acid according to claim 2.

6. The hydrochloride of a N-phosphonomethylglycylhydroxamic acid according to claim 2.

7. The copper salt of a N-phosphonomethylglycylhdroxamic acid according to claim 2.

8. The isopropylammonium salt of a N-phosphonomethylglycylhydroxamic acid according to claim 2.

* * * * *